(12) United States Patent
Butterfield

(10) Patent No.: US 8,096,186 B2
(45) Date of Patent: Jan. 17, 2012

(54) SYSTEMS AND METHODS FOR MEASURING FLUID PRESSURE WITHIN A DISPOSABLE IV SET CONNECTED TO A FLUID SUPPLY PUMP

(75) Inventor: Robert D. Butterfield, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 135 days.

(21) Appl. No.: 12/731,001

(22) Filed: Mar. 24, 2010

(65) Prior Publication Data

US 2011/0232388 A1    Sep. 29, 2011

(51) Int. Cl.
*G01L 9/12* (2006.01)

(52) U.S. Cl. ............... 73/714; 73/718; 73/724

(58) Field of Classification Search ............ None
See application file for complete search history.

(56) References Cited

U.S. PATENT DOCUMENTS

| | | | |
|---|---|---|---|
| 4,287,553 A * | 9/1981 | Braunlich | 361/283.4 |
| 4,336,800 A | 6/1982 | Pastrone | |
| 4,557,725 A | 12/1985 | Heyne et al. | |
| 4,944,187 A * | 7/1990 | Frick et al. | 73/718 |
| 5,000,049 A | 3/1991 | Cooper et al. | |
| 5,400,489 A * | 3/1995 | Hegner et al. | 29/25.41 |
| 5,813,280 A | 9/1998 | Johnson et al. | |
| 5,992,240 A * | 11/1999 | Tsuruoka et al. | 73/718 |
| 6,981,960 B2 | 1/2006 | Cho et al. | |
| 7,107,837 B2 | 9/2006 | Lauman et al. | |
| 7,311,691 B2 | 12/2007 | Cartledge et al. | |
| 7,448,276 B2 | 11/2008 | Crockett et al. | |
| 7,553,295 B2 | 6/2009 | Susi | |
| 2009/0151463 A1 | 6/2009 | Recio et al. | |

OTHER PUBLICATIONS

International Search Report and Written Opinion tor PCT/US2011/027908 mailed Oct. 25, 2011.

* cited by examiner

*Primary Examiner* — Andre Allen
(74) *Attorney, Agent, or Firm* — McDermott Will & Emery LLP

(57) ABSTRACT

Systems and methods of measuring pressure of fluid in a disposable IV set connected to a fluid supply pump is disclosed. At least one sensing arrangement coupled to the fluid supply pump is provided. A chamber having a movable element is provided, the movable element configured to move in response to changes in fluid pressure within the disposable IV set and thereby cause a change in a sensed measurement variable associated with the sensing arrangement without contacting the sensing arrangement. A measuring signal indicative of the sensed measurement variable is generated. The fluid pressure within the disposable IV set is determined based on the measuring signal.

34 Claims, 8 Drawing Sheets

SYSTEMS AND METHODS FOR MEASURING FLUID PRESSURE WITHIN A DISPOSABLE IV SET CONNECTED TO A FLUID SUPPLY PUMP

FIELD

The present disclosure relates to pressure sensing, and, in particular, to systems and methods for measuring fluid pressure within a disposable IV set connected to a fluid supply pump.

BACKGROUND

Liquid supply pumps are used extensively in medical and other fields. In medical fields, for example, the use of intravenous (IV) pumps for delivery of fluids, such as medications and nutrient solutions, has been a wide-spread practice in hospitals. IV pumps have gained widespread acceptance because they are able to deliver IV fluids under accurate and tightly controlled conditions so that medications and the like can be delivered intravenously to a patient wherein deviations from a desired delivery rate can have harmful consequences.

An IV pump device is often provided with a pumping mechanism that is adapted to accept a cassette containing a pumping chamber. The cassette is typically designed for one use only, and needs to be economically manufactured to reduce its cost. The cassette is typically activated by a reciprocatory (e.g., peristaltic) driving force of the pumping mechanism and has a fluid inlet for connecting to a tube leading to the supply container and a fluid outlet for connecting to a tube that delivers the IV fluid to the patient.

For control and monitoring purposes, it is desirable to measure the fluid pressure within the disposable IV cassette. For example, the fluid pressure signal can be used to detect, inter cilia, an empty supply bottle, an occluded intake or outlet path, a bottle-channel association, the fluid level in the bottle and the flow resistance of the fluid pathway. One challenge is to provide a pressure sensing system for measuring the fluid pressure within the cassette that is both economical and accurate. Ideally the sensor accurately measures both positive and negative pressures, negative pressures commonly arising due to elevation of the patient of container with respect to the sensor element. High resolution on the order of 1 mmHg is needed as well for the purposes mentioned above.

Conventionally, the fluid pressure within a cassette is measured by a contact measurement method in which the cassette or an object attached to the cassette physically contacts a sensing arrangement (e.g., a resistive strain gauge force sensor) to exert a contact pressure/force on the sensing arrangement. In such contact-based pressure sensing systems, the sensing arrangement is typically intentionally preloaded with a positive pressure/force such as exerted by a deformed tubing wall in order to artificially bias a zero-pressure point so that a negative pressure can be measured. One problem with such a positive-biasing scheme with a preloaded sensing arrangement is that the preloading force can diminish over time due to stress relaxation resulting in the related biasing point drifting downward over time. This may cause underestimation of true fluid pressure.

SUMMARY

Embodiments described herein address the above-discussed problem associated with the contact-based pressure measurement by providing systems and methods for noncontact measurement of fluid pressure within a cassette connected to a fluid supply pump, such as an IV pump. In one aspect, the noncontact pressure sensing involves coupling a sensor base having a non-contacting sensing arrangement to the pump and coupling a movable element having a sensor measurement varying element to an element in the disposable IV set. The sensor measurement element moves in response to changes in fluid pressure within the fluid path and thereby causes a proportionate output signal change from the sensing arrangement. The fluid pressure is determined from a measuring signal indicative of the sensed measurement variable.

Certain embodiments provide a pressure sensing system for measuring fluid pressure within a disposable IV set connected to a fluid supply pump. The system can comprise a sensor base coupled to a pump. The sensor base can have at least one sensing arrangement being stationary with respect to the sensor base. The sensing arrangement can be configured to generate a measuring signal based on a sensed measurement variable. The system can further comprise a measurement circuit electrically connected to the sensing arrangement. The system can further comprise an element within the disposable IV set configured for placement in near proximity with the sensor base. The disposable component can have a fluid inlet and a fluid outlet, and a movable element to move with changes in fluid pressure within the cassette. The amount of movement of the movable element can be related to the amount of change in fluid pressure. The system can further comprise a sensor measurement varying element coupled to move with the movable element by a non-contacting sensing field such as light or other electromagnetic fields. The sensor measurement varying element can thereby cause a change in the sensed measurement variable without contacting the sensing arrangement.

Certain embodiments provide for a cassette configured for attaching to a fluid supply pump. The cassette can comprise a pumping chamber having a fluid inlet and a fluid outlet and configured to receive a fluid from a fluid storage unit via the fluid inlet. The cassette can further comprise a diaphragm structure coupled to the pumping chamber, the diaphragm structure comprising a movable element configured to move with changes in fluid pressure within the pumping chamber and thereby cause a change in a sensed measurement variable sensed by at least one sensing arrangement coupled to the fluid supply pump without contacting the sensing arrangement, the amount of movement of the movable element being related to the amount of change in fluid pressure.

Certain embodiments provide a method of measuring pressure of fluid in a disposable IV set connected to a fluid supply pump. The method can comprise providing at least one sensing arrangement coupled to the fluid supply pump. The method can further comprise providing a chamber having a movable element configured to move with the movable element in response to changes in fluid pressure within the disposable IV set and thereby cause a change in a sensed measurement variable associated with the sensing arrangement without contacting the sensing arrangement. The method can further comprise generating a measuring signal indicative of the sensed measurement variable. The method can further comprise determining the fluid pressure within the disposable IV set based on the measuring signal.

Certain embodiments provide a pressure sensing system for measuring fluid pressure within a disposable IV set connected to a fluid supply pump. The system can comprise a sensor base coupled to a pump. The sensor base can have at least one sensing arrangement being stationary with respect to the sensor base. The sensing arrangement can be configured to generate a measuring signal based on a sensed measurement variable. The system can further comprise a measurement circuit electrically connected to the sensing arrangement. The system can further comprise an element within the disposable IV set configured for placement in near proximity with the sensor base. The disposable component can have a fluid inlet and a fluid outlet, and a movable element to move with changes in fluid pressure within the cassette. The amount of movement of the movable element can be related to the amount of change in fluid pressure. The system can further comprise a sensor measurement varying element coupled to move with the movable element by a non-contacting sensing field such as light or other electromagnetic fields. The sensor measurement varying element can thereby cause a change in the sensed measurement variable without contacting the sensing arrangement.

Certain embodiments provide a disposable pressure sensing element configured for attaching to a fluid supply pump. The element may serve only for sensing of pressure or may be combined with other features such as a pumping chamber having a fluid inlet and a fluid outlet. The sensing element can be configured to receive a fluid from a fluid storage unit via the fluid inlet. The sensing element can further comprise a diaphragm structure. The diaphragm structure can comprise a movable element configured to move with changes in fluid pressure within the fluid delivery path. The amount of movement of the movable element can be related to the amount of change in fluid pressure. The disposable pressure sensing element can further be designed to provide a varying physical quality such as position to a non-contacting sensor measurement element. The sensor measurement varying element can thereby cause a change in a sensed measurement variable detectable by at least one sensing arrangement coupled to the fluid supply pump without contacting the sensing arrangement.

Certain embodiments provide a method of measuring fluid pressure within a disposable pressure sensing element or combined within a multi-functional disposable cassette connected to a fluid supply pump. The method can comprise providing at least one sensing arrangement coupled to the fluid supply pump. The method can further comprise providing a movable element coupled to the cassette and having a sensor measurement varying element. The sensor measurement varying element can be coupled to move with the movable element in response to changes in fluid pressure within the cassette and thereby cause a change in a sensed measurement variable associated with the sensing arrangement without contacting the sensing arrangement. The method can further comprise generating a measuring signal indicative of the sensed measurement variable. The method can further comprise determining the fluid pressure within the cassette based on the measuring signal.

It is to be understood that both the foregoing summary and the following detailed description are exemplary and explanatory and are intended to provide further explanation of the embodiments as claimed.

BRIEF DESCRIPTION OF THE DRAWINGS

The accompanying drawings, which are included to provide further understanding of the invention and are incorporated in and constitute a part of this specification, illustrate disclosed embodiments and together with the description serve to explain the principles of the disclosed embodiments.

DETAILED DESCRIPTION

In the following detailed description, numerous specific details are set forth to provide a full understanding of the disclosed and claimed embodiments. It will be apparent, however, to one ordinarily skilled in the art that the embodiments may be practiced without some of these specific details. In other instances, well-known structures and techniques have not been shown in detail to avoid unnecessarily obscuring the disclosure.

The word "exemplary" is used herein to mean "serving as an example, instance, or illustration." Any embodiment or design described herein as "exemplary" is not necessarily to be construed as preferred or advantageous over other embodiments or designs.

Various embodiments of the present disclosure address and solve problems associated with conventional systems and methods of measuring fluid pressure inside a cassette which rely on a positive biasing in order to measure negative as wells as positive fluid pressures. Certain embodiments of the present disclosure provide a noncontact pressure sensing system for measuring fluid pressures within a cassette connected to a fluid supply pump. A sensor base having at least one sensing arrangement is coupled to the pump, and a movable element having a sensor measurement varying element is coupled to the cassette. The measurement varying element moves with changes in fluid pressure within the cassette, and thereby causes a change in a sensed measurement variable (e.g., capacitance, light intensity, and magnetic field) without contacting the sensing arrangement. The pressures sensing element may be embodied within a multi-functional sterile disposable 'cassette' or within a single purpose housing used solely for the measurement of pressure.

Figure 1:
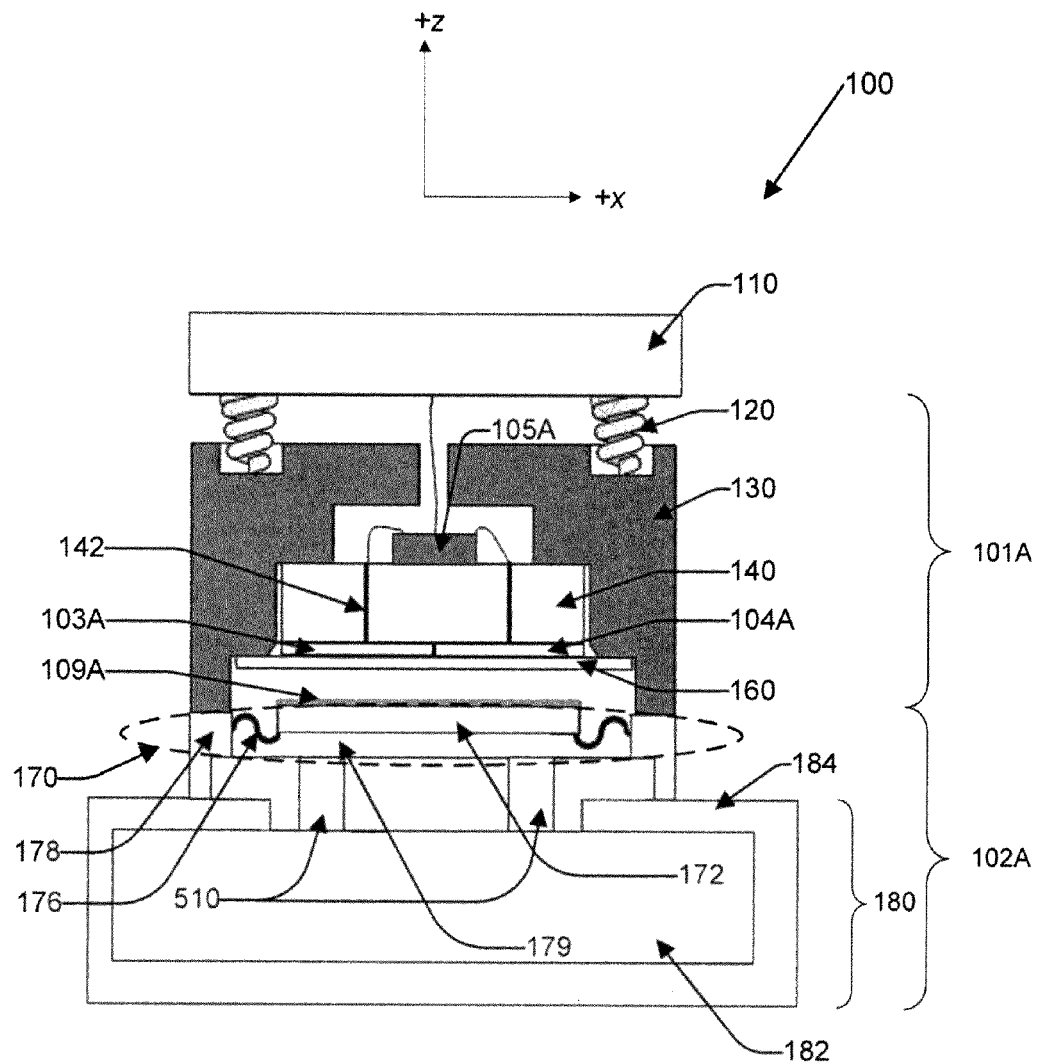
FIG. 1 is a cross-sectional view of an exemplary capacitive-type noncontact pressure sensing system 100 that is based on capacitance as a sensed measurement variable according to certain embodiments.
Figure 2:
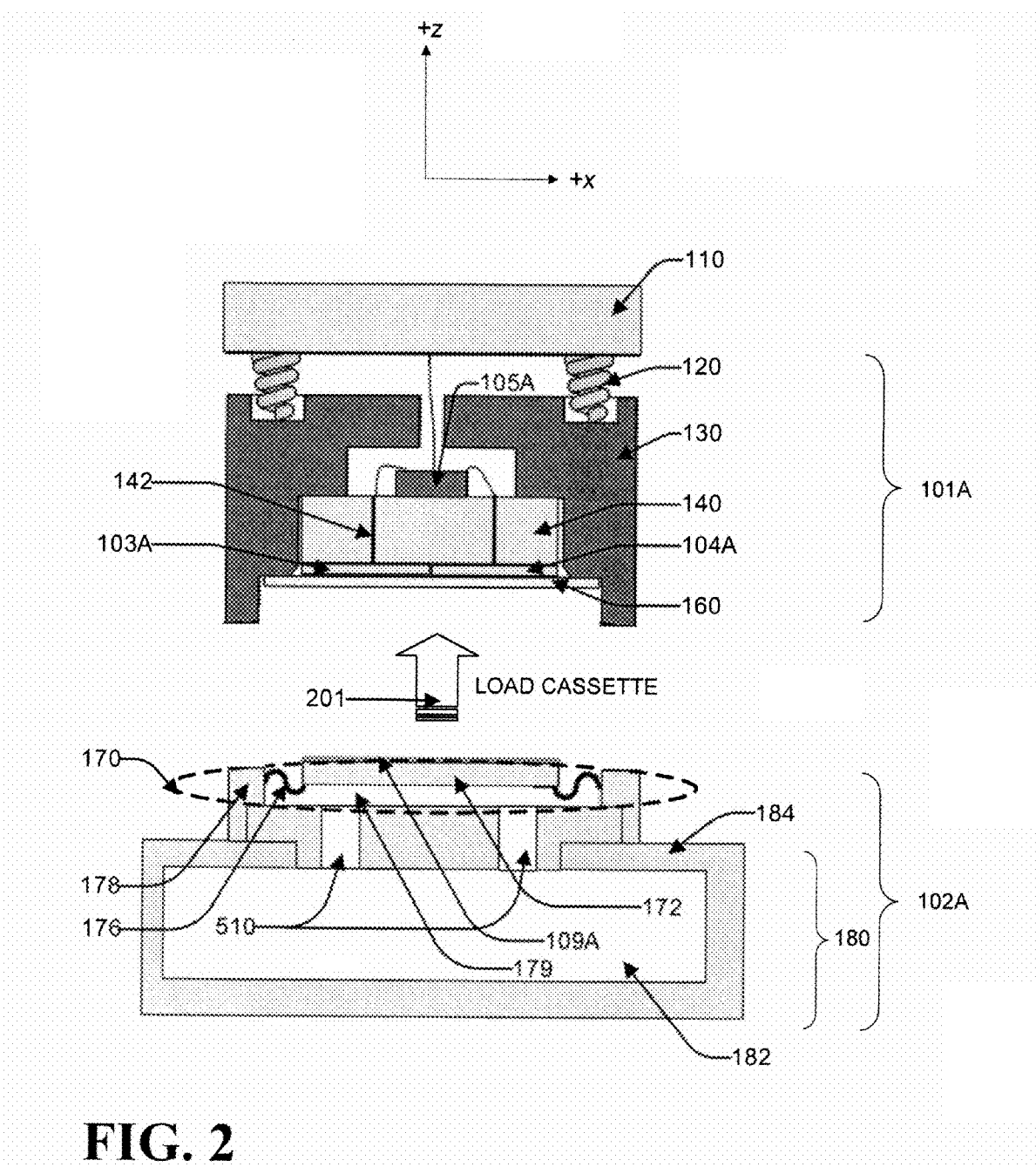
FIG. 2 is a diagram of the exemplary capacitive-type noncontact pressure sensing system of FIG. 1 shown with the cassette separated from the sensor base.

FIG. 1 is a cross-sectional of an exemplary capacitive-type noncontact pressure sensing system 100 that is based on capacitance as a sensed measurement variable according to certain embodiments. The system 100 includes a sensor base 101A coupled to a pump body 110, and a cassette 102A. The cassette 102A is configured for attaching or loading to the pump or, more particularly, to the sensor base 101A. Conventional connecting structure may be employed for attaching the cassette 102A to the sensor base 101A, such as a releasable snap connection. FIG. 1 shows the sensor base 101A and the cassette 102A in an attached or loaded state, and FIG. 2 show the sensor base 101A and the cassette 102A in a separated or unloaded state with an arrow 201 indicating the loading or connection of the cassette 102A to the sensor base 101A. In the illustrated example, the sensor base 101A includes a spring-loaded frame structure 130 and a printed circuit (PC) substrate 140. The spring-loaded frame structure 130 is connected to the pump body 110 via springs 120 and holds the PC substrate 140 stationary with respect to the rest of the sensor base 101A.

Figure 3:
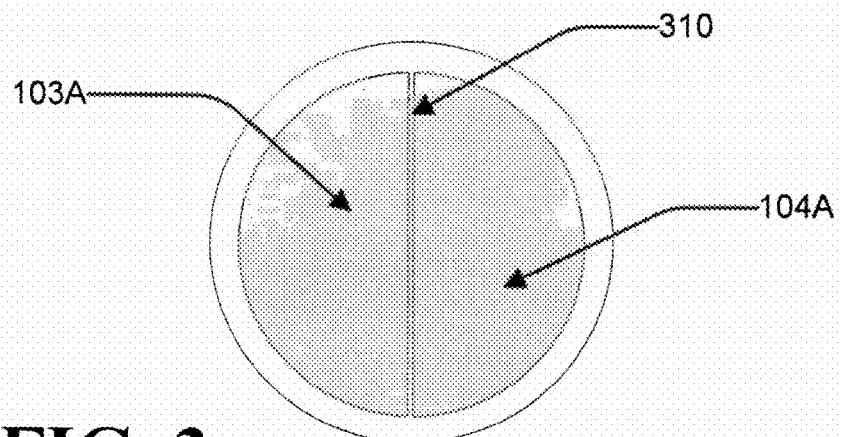
FIG. 3 is a bottom-up view of a printed circuit substrate showing the first and second plates formed on the substrate.

The PC substrate 140 has a first plate 103A and a second plate 104A formed (e.g., deposited and patterned) on a bottom side of the PC substrate 140 facing the cassette 102A, and a measurement circuit 105A disposed on the top side of the PC substrate 140. The first and second plates 103A, 104A constitute sensing elements or arrangements for the capacitive-type noncontact pressure sensing system 100. FIG. 3 is a bottom-up view (e.g., in the +z direction) of the PC substrate 140 showing the first and second plates 103A, 104A. In the illustrated example, the first and second plates 103A, 104A are two semicircular shaped plates separated by a small (e.g., 0.005 inch) insulating gap 310. Alternatively, one or both first and second plates 103A, 104A can have different shapes including, but are not limited to, rectangles, triangles, full circles, and a circle and an annular ring surrounding the circle.

Returning to FIG. 1, the first and second plates 103A, 104A are electrically connected to a measurement circuit 105A through conductor-coated via holes 142 provided in the PC substrate 140. In certain embodiments, the measurement circuit 105A includes a sensor measurement IC such as an Analog Devices AD7754 and the like with the ability to measure differential capacitances. Alternatively, the measurement circuit 105A may comprise a plurality of discrete analog and/or digital components providing signal excitation and signal conditioning functions, for example. In the illustrated example, the sensor base 101A further includes a thin insulating layer 160 comprising an insulating material, such as Mylar or Parylene, to cover the first and second plates 103A, 104A so as to provide protection from electrostatic discharge damages to the measurement circuit 105A and other electronic components.

The cassette 102A includes a cassette body 180 and a diaphragm structure 170 coupled to the cassette body 180. The cassette body 180 includes a pumping chamber 182 and a wall 182 for the pumping chamber 182. Although not shown in the portion shown in FIG. 1, the cassette body 180 further includes a fluid inlet leading to a supply container for receiving the fluid into the pumping chamber 182, and a fluid outlet leading the fluid out to a receiving device or party (e.g., a patient).

The diaphragm structure 170 includes a movable element 172, a deformable element 176, and a side wall 178. In the illustrated example, the movable element 172 is a flat disc. The movable element 172 is coupled to the side wall 178 via the deformable element 176 coupled to the perimeter of the movable element 172 on one side and to an inner perimeter of the side wall 178 on the other side. The diaphragm structure 170 also includes a cavity 179 that is configured to receive fluid from the cassette body 180 (e.g., the pumping chamber 182).

Figure 4:
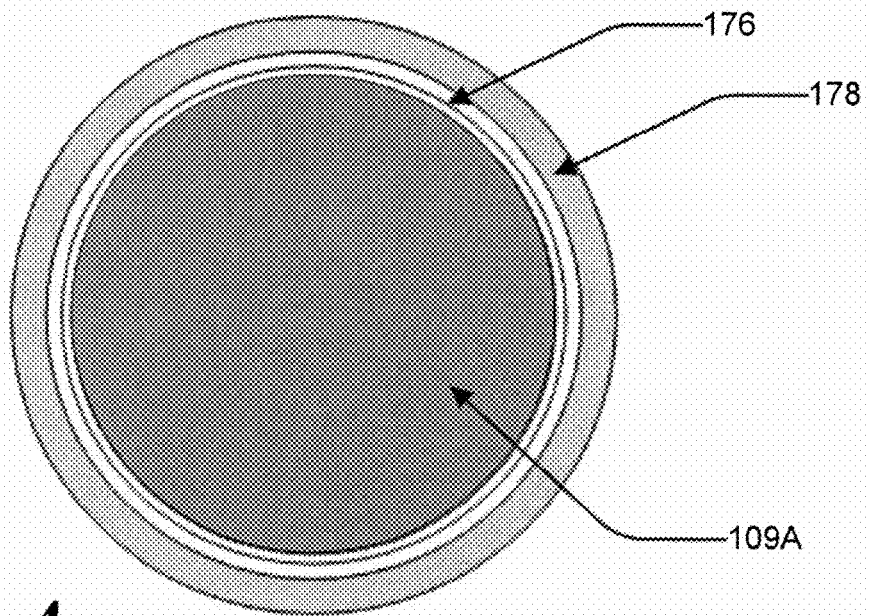
FIG. 4 is a top-down view of a diaphragm structure showing a conductive layer formed over a movable element of the diaphragm structure.
Figure 6:
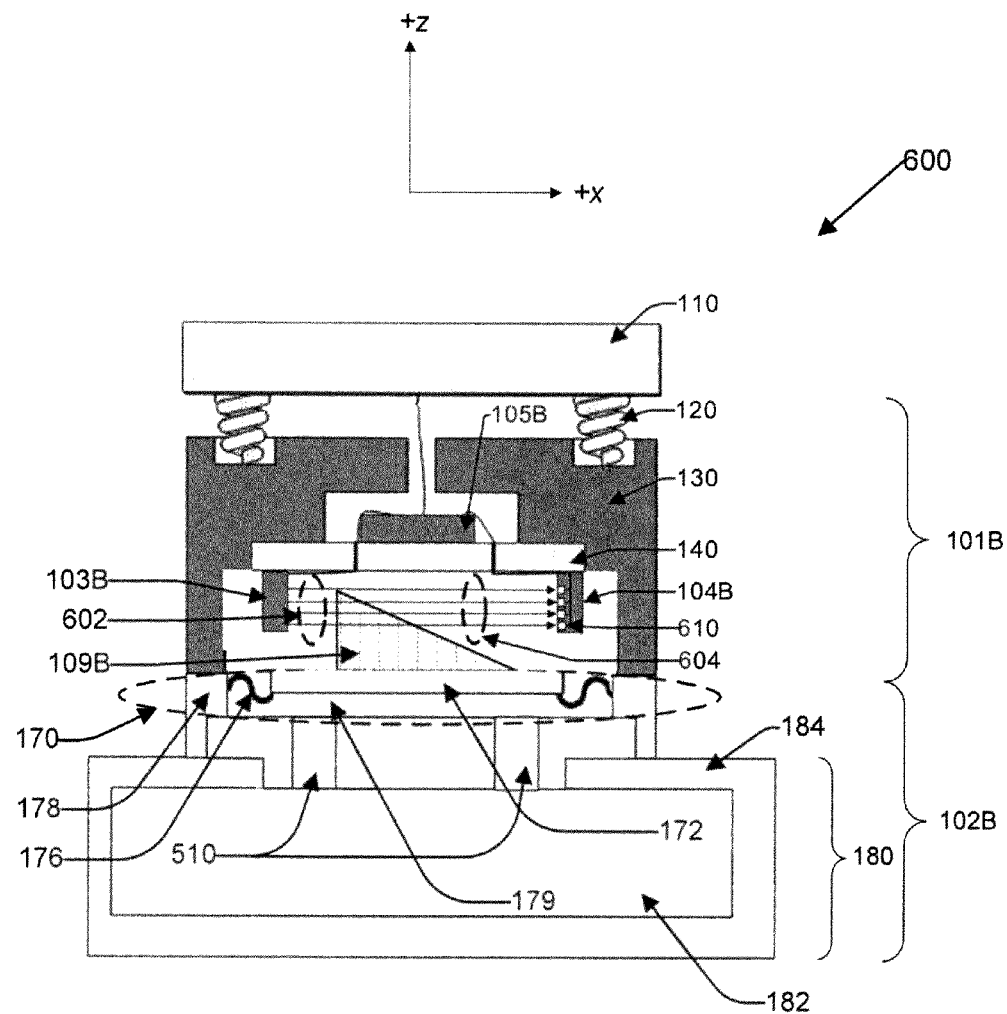
FIG. 6 is a cross-sectional view of an exemplary optical-type noncontact pressure sensing system that is based on light intensity as the sensed measurement variable according to certain embodiments.
Figure 7:
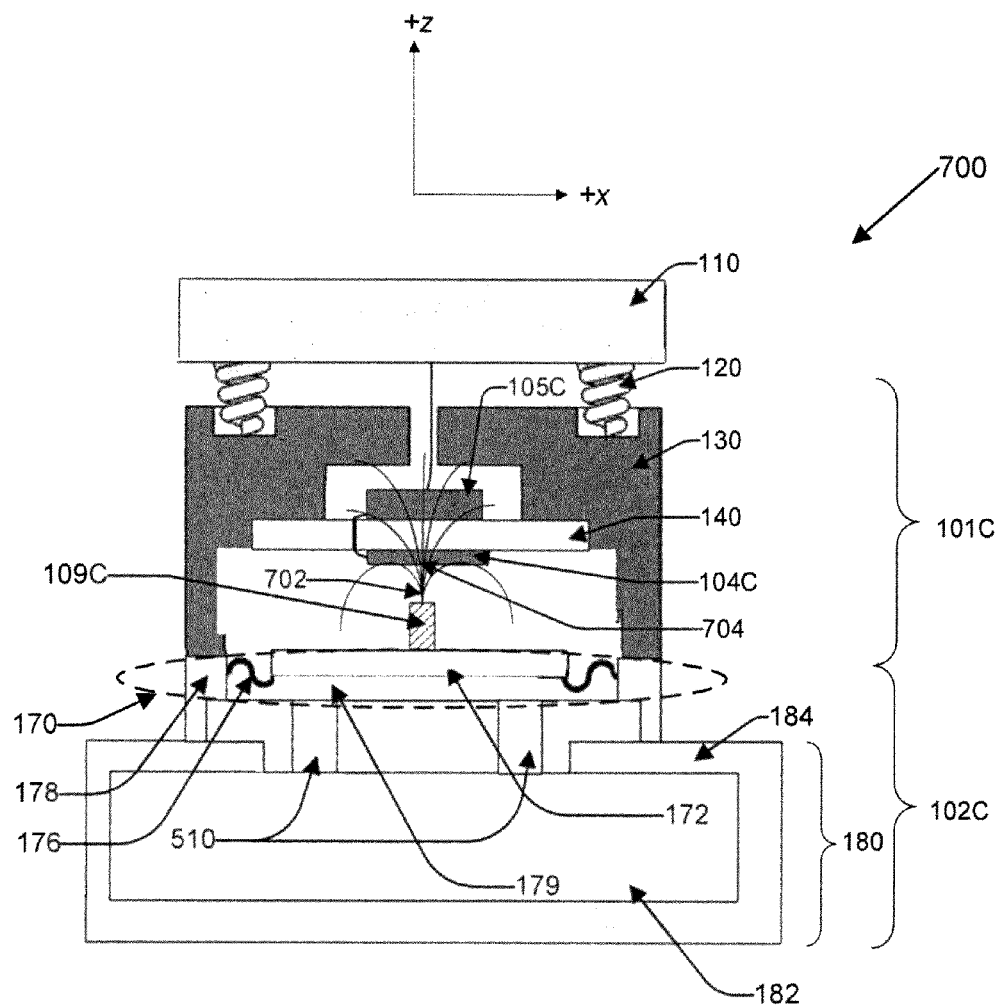
FIG. 7 is a cross-sectional view of an exemplary magnetic-type noncontact pressure sensing system that is based on magnetic field as the sensed measurement variable according to certain embodiments.

The cassette 102 further includes a conductive layer 109A formed over (e.g., deposited or coated on, affixed or bonded to) the disc 172. FIG. 4 is a top-down view (e.g., in the −z direction) of the diaphragm structure 170 showing a conductive layer 109A formed over the movable element 172 of the diaphragm structure. As will be discussed more below, the conductive layer 109A constitutes a sensor measurement varying element of the capacitive-type noncontact sensing system 100. As used herein, the term "sensor measurement varying element" refers to a structure, a device, a layer, or a feature that can be coupled with a movable element (e.g., the disc 172) to move relative to one or more sensing arrangements (e.g., the first and second plates 103A, 104A) in response to changes in fluid pressure within the cassette and thereby cause a corresponding change in a sensed measurement variable (e.g., capacitance between the first and second plates 103A, 10313). Examples of other sensor measurement varying elements include an optical attenuator employed in an optical-type noncontact pressure sensing system (FIG. 6), and a magnet for use in a magnetic-type noncontact pressure sensing system (FIG. 7). The illustrated embodiments are exemplary only, as other types of noncontact pressure sensing systems may be employed.

Figure 5:
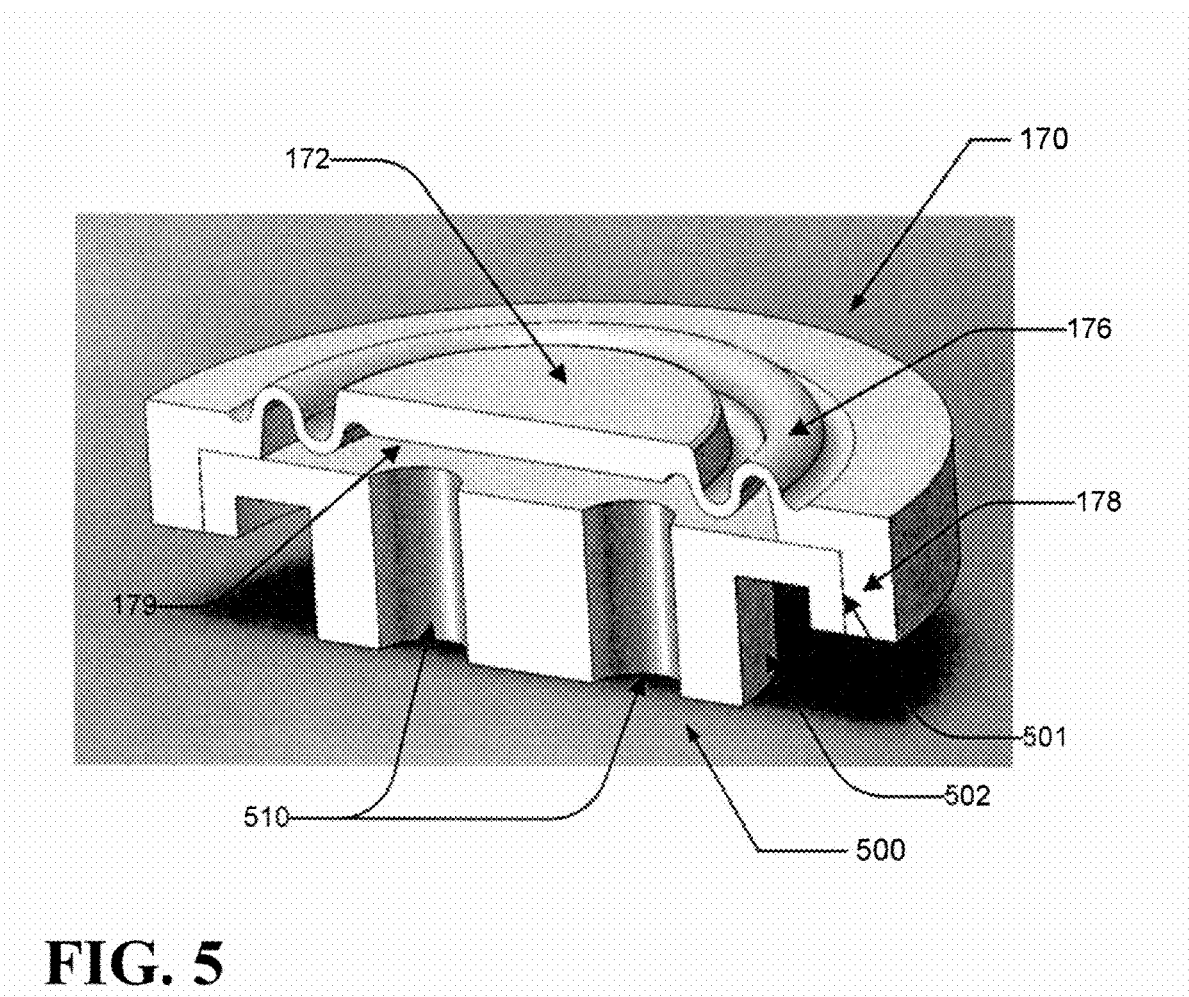
FIG. 5 is a perspective cross-sectional view of the diaphragm structure and a coupler configured to couple the diaphragm structure to the cassette according to certain embodiments.

FIG. 5 is a perspective cross-sectional view of the diaphragm structure 170 and a coupler 500 for coupling the diaphragm structure to the cassette body 180 (FIG. 1) according to certain embodiments. In certain embodiments, the coupling comprises placing the sensing element in proximity to a detector apparatus within the pump. For clarity, the diaphragm structure 170 is shown without a sensor measurement varying element (e.g., the conductive layer 109A) disposed over the movable element 172. The deformable element 176 is connected between outer circumference of the movable element 172 and the inner circumference of the side wall 178. The deformable element 176 is configured to deform in response to changes in the fluid pressure within the cassette 102A, or more specifically, within the pumping chamber 182 of the cassette body 180, and thereby cause the movable element 172 to move in the +z direction if the pressure is increasing or in the −z direction if the pressure is decreasing. In the illustrated example, the cross-section of the deformable element 176 has an "S" or "sigmoid" shape, but the cross-section may have another shape such as a thin rectangle, a curvilinear shape, a "Z" shape, or a "U" shape.

In certain embodiments, the movable element 172 is non-flexing, meaning the movable element does not flex or deform when subjected to a nonzero fluid pressure. In those embodiments, only the deformable element 176 flexes or deforms when subjected to a nonzero fluid pressure. The movable element 172 and the deformable element 176 can be made to have different flexibility or deformability (e.g., the former nonflexing and the latter flexing) by making them with, for example, different materials, different thicknesses, and/or different cross-sectional shapes. In one aspect, the use of a nonflexing movable element is advantageous because there is less net volume change during the pressure measurement. In other words, having the nonflexing stiff moving member helps to minimize the compliance value, e.g., down to about 0.1 μL/mmHg. The low compliance for a pressure sensor means the act of pressure measurement has a low effect on the state of the measurand, namely the fluid pressure as well as the fluid displacement itself. In addition, the nonflexing movable element can better preserve the structural integrity of the sensor measurement varying element such as the conductive layer 109A attached to the movable member. For example, a conductive layer that is coated on a flexing movable member can be detached or peeled off from the movable member after repeated flexing of the movable member. In addition, the use of the nonflexing movable element in the present embodiments can also result in a more controlled, linear, and repeatable sensitivity (change in displacement per unit change in pressure). In other embodiments, both the deformable element 176 and the movable element 172 are made to flex or deform when subjected to a nonzero fluid pressure. In yet other embodiments, a flexible/deformable movable element is connected directly to the side wall 178 without having a deformable element in between.

Also, in the illustrated example, the movable element 172, the deformable element 176, and the side wall 178 are formed with a same material, such as a polycarbonate, in a single mold. Alternatively, the movable element 172, the deformable element 176, and the side wall 178 are made of two or more different materials and are co-molded together. In certain ones of such embodiments, the movable element 172 and the side wall 178 are made of a polycarbonate material while the deformable element is made of a thermoplastic elastomer for flexibility. In yet other embodiments, the movable disk 172 is made of a metal and functions as the conductive layer 109A, thereby eliminating the need for a separate conductive layer.

Referring now to FIG. 5, the coupler 500 is configured to couple or connect the diaphragm structure 170 to the cassette body 180 or, more specifically, to the pumping chamber 182, both fluidically and mechanically. In the illustrated example, the coupler 500 includes a first outer wall 501 and a second outer wall 502. The first outer wall 501 is used to form a sealed mechanical coupling (e.g., a press fit) between the coupler 500 and the diaphragm structure 170. The second outer wall 502 is used to form a sealed mechanical coupling between the diaphragm-coupler composite structure and the cassette body 180 (FIG. 1). In the illustrated embodiment, the second outer wall 502 is inserted (e.g. pressure fitted) into an aperture formed in the wall 184 of the pumping chamber 182 (FIG. 1). The coupler 500 also includes openings 510 for establishing a fluidic connection between the cavity 179 and the pumping chamber 182 and equalizing the fluid pressure therebetween.

In operation, the cassette 102A is loaded or connected to the sensor base 101A as indicated by the arrow 201 of FIG. 2. When the cassette 102A is initially mated with the sensor base 101A, the springs 120 are compressed and exert a restoring force (e.g., in the −z direction) against the cassette 102A via the frame structure 130. This spring-loading arrangement avoids most mechanical tolerance stack-up errors and noises created by relative movement between the sensor base 101A and the cassette 102A. At this stage, there is no net pressure inside the cavity 109, and there is no net force exerted on the movable element 172. The movable element 172 is therefore at its zero-pressure quiescent point. After the cassette 102A is mated with the base 110A and a fluid (e.g., liquid medication) is introduced into the pumping chamber 182 of the cassette 102A, the cavity 179 receives a portion of the fluid through the openings 510 in the coupler 500 (FIG. 5). The fluid pressure within the cavity 179 is thereby made to be substantially the same as the fluid pressure within the pumping chamber 182 (with a possible small DC offset). The fluid pressure (positive or negative) within the cavity 179 exerts force (positive or negative) on the movable element 172 and causes movement of the movable element 172. For example, if the pressure is positive, the movable element 172 moves in the +z direction from the zero-pressure quiescent point towards the first and second plates 103A, 104A. On the other hand, if the pressure is negative, the movable element 172 moves in the −z direction from the zero-pressure quiescent point away from the first and second plates 103A, 104A. The positive pressure, therefore, causes the conductive layer 109A, which is coupled to the movable element 172, to move closer to the first and second plates 103A, 104A and results in an increased capacitance between the two plates 103A, 104A. On the other hand, negative pressure causes the conductive layer 109A to move away from the first and second plates 103A, 104A and results in a reduced capacitance between the two plates 103A, 104A.

The measurement circuit 105A is configured to measure the capacitance between the first and second plates 103A, 104A and provide a measuring signal indicative of the capacitance. This can be achieved in one of many known methods of measuring capacitance including differential capacitance measurement involving one or more fixed reference capacitors. Integrated circuits (ICs) that are designed for such differential capacitance measurements are commercially available, an example being Analog Devices AD7754. Some of such application-specific ICs may output digital data indicative of the measured capacitance. Alternatively, an IC or a combination of discrete analog/digital components designed for capacitance measurement may output an analog measuring signal which then can be converted into digital data for use by a processor by an analog-to-digital converter. A processor can then receive the digital data indicative of the capacitance and determine the fluid pressure within the cassette from a known relationship between the two quantities —either an equation or a lookup table that can account for a nonlinearity in the capacitance versus fluid pressure response. The equation and the lookup table can also account for any pre-established DC pressure offset between the fluid pressure within the pumping chamber 182 and the fluid pressure within the cavity 179. The result is an accurate and repeatable noncontact measurement of both positive and negative fluid pressures within the cassette (e.g., the pumping chamber 182) without preloading of the sensing arrangement and related biasing of a zero-pressure point.

While the discussion above has focused on capacitance as the sensed measurement variable, it shall be appreciated by those skilled in the art in view of the present disclosure that various alternative embodiments may be employed without departing from the scope of the present disclosure. For example, FIG. 6 is a cross-sectional view of an exemplary optical-type noncontact pressure sensing system 600 that is based on light intensity as the sensed measurement variable according to certain embodiments. The illustrated optical-type noncontact pressure sensing system 600 of FIG. 6 shares many structural elements with the illustrated capacitive-type noncontact pressure sensing system 100 of FIG. 1, and the descriptions for the shared elements will not be repeated. Instead, the following description focuses on comparing and contrasting the two pressure sensing systems.

In the illustrated example of FIG. 6, the optical-type noncontact pressure sensing system 600 employs a light source 103B and a light detector 104B as the sensing arrangements, and an optical attenuator 109B as the sensing measurement varying element. The light source 103B may be a laser or a non-laser light source such as an LED. The light detector 104B can include one or more photosensing elements, such as photodiodes or photoresistors, that are capable of providing an indication of an intensity of light received in the form of a change in current or resistance, for example. In the illustrated example, the light detector 104B includes a vertical array of photosensing elements 610 for the purpose of providing an integral noise-averaging of received light intensities. However, in alternative embodiments, the light detector 104B contains only one photosensing element, and the noise-averaging is performed through repeated measurements. As with the conductive layer 109A in the capacitive-type noncontact pressure sensing system 100, the optical attenuator 109B is coupled to (e.g., attached to, bonded on, fixed to, integrated with) the movable element 172 so that the optical attenuator 109B moves in concert with the movable element 172 with changes in fluid pressure within cassette 102B. The optical attenuator 109B can comprises an optically absorptive material (e.g. a structural plastic such as polycarbonate, isoplast, acrylic, and the like that can be made opaque with addition of colorants) that has relatively high absorbance values.

In operation, the optical attenuator 109B receives incident light beams 602 emitted by the light source 103B and transmits attenuated light beams 604. Depending on the relative positions of the sensing arrangements and the optical attenuator 109B, at certain pressures, an upper portion of the incident light beams 602 may not even pass through the optical attenuator 109B. The attenuated light beams 604 (and possibly an unattenuated portion of the incident light beams 602) are received by the vertical array of photosensing elements 610 and provide measuring signals. A measuring circuit 105B receives measuring signals from individual photosensing elements and sums the measuring signals either in the analog domain or in the digital domain. Alternatively, the summing of the measuring signals (e.g., photocurrents) id performed physically within the light detector 104B to produce a summed measuring signal, and the measuring circuit 105B receives and processes the summed measuring signal. Regardless of the choice of the mechanism, the summing of the measuring signals from the multiple photosensing elements 610 provides an integral noise-averaging of the received light intensities, each of which can have a significant noise component relating to intrinsic thermal noise and noise relating to external factors such as the vibration of the optical attenuator 10913, and thereby enhances the accuracy and repeatability of the fluid pressure measurement.

In the illustrated example of FIG. 6, thickness of the optical attenuator 109B in the light-travel direction (e.g., the x-direction thickness) varies along the movement direction of the movable element 172 (e.g., the z direction). Accordingly, the greater the +z direction movement of the movable element (corresponding to an increase in the fluid pressure within the cassette), the greater the net attenuation of the incident light beams 602 by the optical attenuator 109B and hence the less light intensities received by the light detector 104B. Conversely, the less the +z direction movement of the movable element (corresponding to a decrease in the fluid pressures within the cassette), the less the net attenuation of the incident light beams 602 by the optical attenuator 109B and hence the greater the light intensities received by the light detector 104B. Accordingly, in the particular illustrated arrangement, the sensed measurement variable—the received light intensities—has a negative or inverse relationship with respect to the fluid pressures within the cassette 102B. However, it shall be appreciated by those skilled in the art in view of the present disclosure that the particular arrangement and the resulting inverse relationship is provided for illustration purposes only, and other arrangements and other relationships are possible without departing from the scope of the present disclosure. For example, the optical attenuator 109B may be an inverted trapezoid with the shorter side attached to the movable element 172, in which case the received light intensities would have a direct or positive linear relationship with respect to the fluid pressure within the cassette 102B.

In the illustrated example, the attenuation variation by the optical attenuator 109B along the z direction is achieved by providing an optical attenuator having a uniform absorbance value throughout in which the x-direction thickness varies along the z-direction. Alternatively, the attenuation variation can be achieved by providing an optical attenuator having a uniform x-direction thickness in which absorbance varies along the z-direction. This can be achieved, for example, by varying the material composition, impurities, or a coating in the z-direction so that the optical attenuator changes from being transparent at one end to being opaque on the other end.

It shall be further appreciated by those skilled in the art in view of the present disclosure that the particular sensing arrangement employed, namely the light source 103B and the light detector 104B aligned along the x-direction to emit and receive light via the optical attenuator 109B, is one of many ways to optically measure the relative movement of the movable element 172, and other arrangements may be employed without departing from the scope of the present disclosure. For example, in an alternative optical-type noncontact pressure sensing system, the pressure sensing is based on the amount of light reflected from a reflective surface coupled to the movable element 172. In such a system, the light source can emit the incident light beams at an incident angle (e.g., $-30°$) and the light detector receives the reflected light beams travelling at a reflected angle (e.g., $+30°$). Depending on the relative positions of the light detector and the reflective surface, the amount of light received at the light detector varies with the maximum amount occurring at the maximum range of the sensing system, for example. This variation can be correlated with the fluid pressure within the cassette. In various optical embodiments, the light control element (e.g., a light attenuator or a reflective surface) is coupled to a movable element that part of a disposable cassette.

FIG. 7 is a cross-sectional of an exemplary magnetic-type noncontact pressure sensing system 700 that is based on magnetic field as the sensed measurement variable according to certain embodiments. As with the optical-type noncontact pressure sensing system 600 of FIG. 6, the illustrated magnetic-type noncontact pressures sensing system 700 shares many structural elements with the illustrated capacitive-type noncontact pressure sensing system 100 of FIG. 1, and the descriptions for the shared elements will not be repeated.

In the illustrated example of FIG. 7, the magnetic-type noncontact pressure sensing system 70 employs a magnetic field sensor 104C as the sensing arrangement, and a magnet 109C as the sensing measurement varying element. The magnetic fields sensor 10C may be any device that is capable of providing an indication of a magnetic field, non-limiting examples of which include a hall-effect sensor, a magnetoresistance (MR) sensor (e.g., the GMR sensor), and a fluxgate magnetometer. The magnet 109C can be any permanent magnet comprising any magnetizable materials including, but are not limited to, iron, nickel, cobalt, some rare earth metals, and some of their alloys (e.g., Alnico). The magnetic field sensor 104C (e.g., a hall-effect sensor) is disposed on the PC substrate 140 and positioned directly above the magnet 109C to measure primarily the z-component of the magnetic field generated by the magnet 109C.

In operation, a magnetic field 702 emanates from the magnet 109C and fills the surrounding region as shown in FIG. 7. The magnetic field sensor 104C senses a local magnetic field 704 and provides a measuring signal indicative of the local magnetic field 704. The measuring signal is measured and processed by a measurement circuit 105C also provided on the PC substrate 140. In certain embodiments, the magnetic sensing function of the magnetic field sensor 104C and the measurement/processing function of the measurement circuit 105C are combined in a single integrated magnetic sensor/measurement IC.

The strength of the z-component of the magnetic field 702 of a bar magnet along the axis falls off inversely with the square of the distance from the magnet. Accordingly, the z-component of the local magnetic field 704 sensed by the magnetic fields sensor 104C varies according to the movement of the movable element 172. The greater the +z direction movement of the movable element 172 (corresponding to an increase in the fluid pressure within the cassette), the less the distance between the magnet 109C and the magnetic field sensor 104C and hence the greater the strength of the z-component of the local magnetic field 704 sensed by the magnetic field sensor 104C. Conversely, the less the +z direction movement of the movable element 172 (corresponding to a decrease in the fluid pressure within the cassette), the greater the distance between the magnet 109C and the magnetic field sensor 104C and hence the less the strength of the z-component of the local magnetic field 704 sensed by the magnetic field sensor 104C. Accordingly, with the particular illustrated arrangement, the sensed measurement variable—the strength of the local magnetic field 104C—has a direct, positive relationship with respect to the fluid pressures within the cassette 102B. However, it shall be appreciated by those skilled in the art in view of the present disclosure that many other arrangements and relationships are possible without departing from the scope of the present disclosure. For example, in alternative embodiments, the bar magnet 109C may be horizontally disposed (e.g., having its axis along x-direction) on the movable element 172 instead of being vertically disposed as shown. In such alternative embodiments, the magnetic field sensor 104C can be configured to measure the strength of the x-component of the local magnetic field 704.

Figure 8:
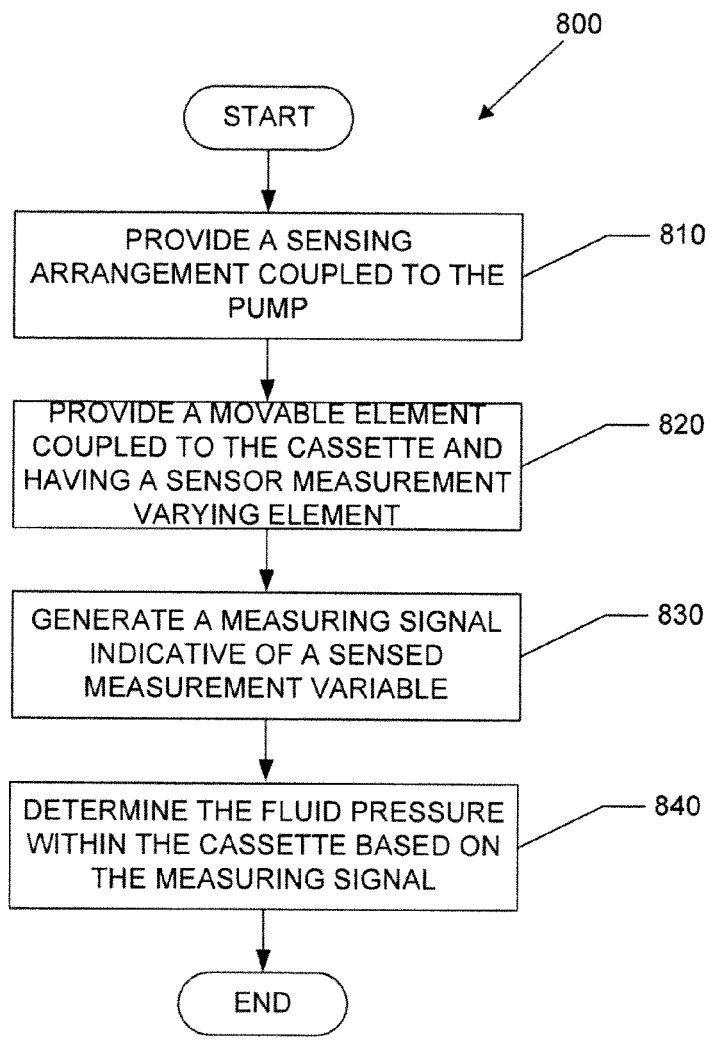
FIG. 8 is a flowchart illustrating an exemplary process for making a noncontact measurement of fluid pressure within a cassette according to certain embodiments.
Figure 9:
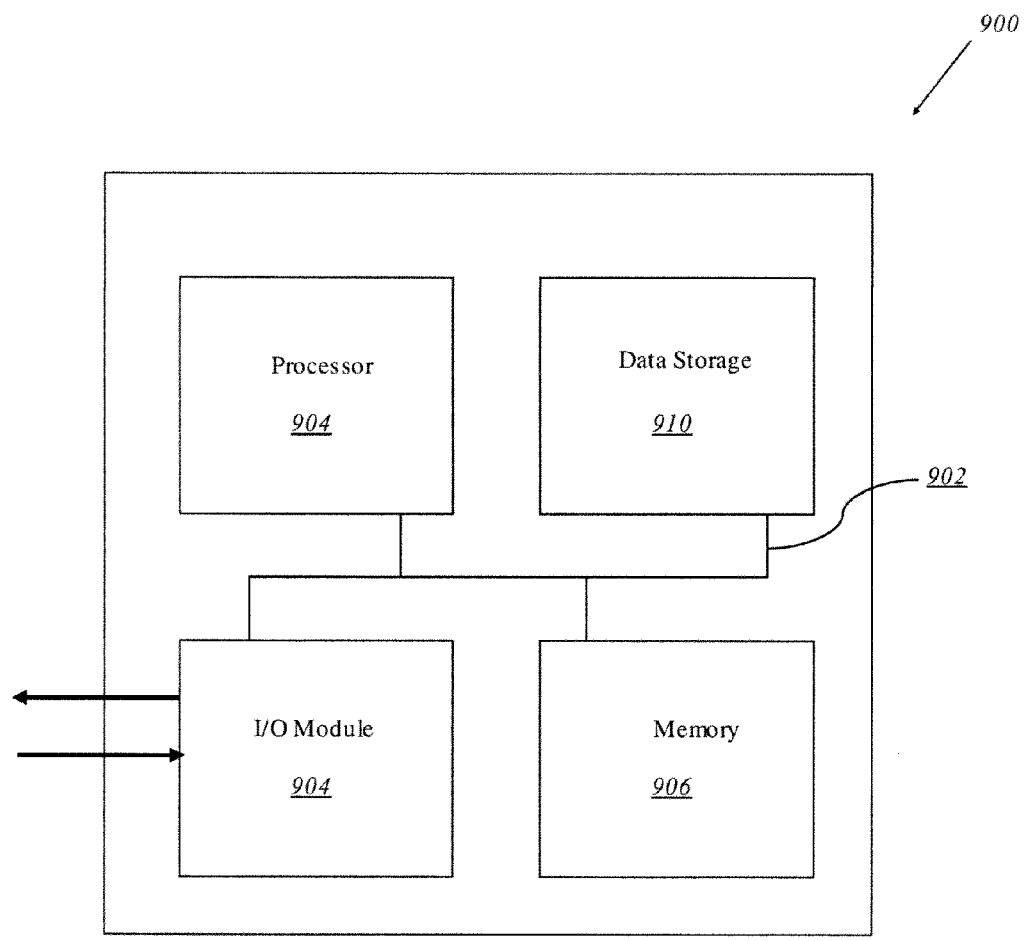
FIG. 9 is a block diagram that illustrates an exemplary computer system upon which certain features of the systems and methods described herein may be implemented.

FIG. 8 is a flowchart illustrating an exemplary process for making a noncontact measurement of fluid pressure within a cassette according to certain embodiments. The process 800 begins at a state 810, in which one or more sensing arrangements coupled to the pump are provided. Examples of the one or more sensing arrangements discussed above include the first and second plates 103A, 104A (FIG. 1), the light source and the light detector 103B, 104B (FIG. 6), and the magnetic field sensor 104C (FIG. 7). Such sensing arrangements are fixed inside the frame element 130 and held stationary with respect to the sensor base 101A,B,C and the pump body 110 during the operation of the pump. The pump can be any fluid supply pump configured for accepting cassettes, including IV pumps for delivering liquid medications and nutrients to patients.

The process 800 proceeds to a state 820, in which a movable element coupled to a cassette is provided. The cassettes can be permanent, semi-permanent, or disposable. In certain embodiments, the cassette is a disposable IV cassette. The movable element is configured to move towards or away from the sensing arrangement (e.g., in +/−z directions —see FIGS. 1, 6, and 7), depending on whether the fluid pressure is increasing or decreasing. The movable element is also configured to move away from the sensing arrangement from its zero-pressure quiescent point. In some embodiments, the movable element is a nonflexing disc that does not flex or deform when subjected to a nonzero fluid pressure. The disc can be part of a diaphragm structure that also includes a deformable portion coupled to the disc at its perimeter. An example of such a diaphragm structure is described in detail above with respect to FIG. 5. A sensor measurement varying element is coupled to move with the movable element in response to changes in fluid pressure within the cassette. The particular choice of the sensor measurement varying element depends on the choice of the sensed measurement variable. Examples of the sensor measurement varying element include (sensed measurement variable in parentheses): the conductive layer 109A (capacitance), the optical attenuator 109B (transmitted light intensities), a reflective layer (reflected light intensities), and the magnet 109C (strength of local magnetic field).

The process 800 proceeds to a state 830, in which a measuring signal indicative of the sensed measurement variable is generated by the sensing arrangement(s) and received and processed by a measurement circuit electrically connected to the sensing arrangement(s). The process 800 proceeds to a state 840, in which the fluid pressure within the cassette is determined based on the measuring signal. In certain embodiments, the fluid pressure is determined by a processor or a computer configured (e.g., programmed) to receive digital data indicative of the sensed measurement variable (e.g., the capacitance, the light intensity, the strength of the local magnetic field) either directly from the sensing arrangement(s) or the measurement circuit or from an analog-to-digital converter receiving an analog measuring signal. The processor can determine the fluid pressure within the cassette by the use of an equation or a lookup table that accounts for a nonlinearity in the sensed measurement variable versus fluid pressure response. The equation and the lookup table can also account for any DC offset between the fluid pressure in the pumping chamber and the fluid pressure in the cavity.

According to certain embodiments, certain aspects of measurements of fluid pressure within the cassette described herein are performed by a computer system 900 in response to processor 904 executing one or more sequences of one or more instructions contained in memory 906. For example, processor 904 can determine the fluid pressure within the cassette from digital data indicative of the sensed measurement variable by executing instructions that involve an equation or a lookup table that accounts for a nonlinearity in the sensed measurement variable versus fluid pressure response. Processor 904 may be a microprocessor, a microcontroller, and a digital signal processor (DSP) capable of executing computer instructions. Such instructions may be read into memory 906 from another machine-readable medium, such as data storage device 910. Execution of the sequences of instructions contained in main memory 906 causes processor 904 to perform the process steps described herein. One or more processors in a multi-processing arrangement may also be employed to execute the sequences of instructions contained in memory 906. In alternative embodiments, hardwired circuitry may be used in place of or in combination with software instructions to implement various embodiments. Thus, embodiments are not limited to any specific combination of hardware circuitry and software.

The term "machine-readable medium" as used herein refers to any medium that participates in providing instructions to processor 904 for execution or storing results of or parameters (e.g., variables or constants) for computations such as for the determination of the fluid pressure within the cassette based on a sensed measurement variable. Such a medium may take many forms, including, but not limited to, non-volatile media, volatile media, and transmission media. Non-volatile media include, for example, optical or magnetic disks, such as data storage device 910. Volatile media include dynamic memory, such as memory 906. Transmission media include coaxial cables, copper wire, and fiber optics, including the wires that comprise bus 902. Transmission media can also take the form of acoustic or light waves, such as those generated during radio frequency and infrared data communications. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, a carrier wave, or any other medium from which a computer can read.

In some embodiments, after processor 904 programmatically determines the fluid pressure within the cassette, the pressure values can be either stored in the machine-readable (not shown) or passed to another program or a subroutine executed the same processor or a different processor for further processing. For example, the fluid pressure in the cassette may be used by another program or subroutine for controlling the flow rate of the medication in an IV pump or for detecting an occlusion or an empty supply container.

The foregoing description is provided to enable any person skilled in the art to practice the various embodiments described herein. While the foregoing embodiments have been particularly described with reference to the various figures and embodiments, it should be understood that these are for illustration purposes only and should not be taken as limiting the scope of the invention.

There may be many other ways to implement the invention without departing from the scope of the present disclosure. For example, certain embodiments described herein can be implemented as "differential" measurement systems in which there is a second detection channel or elements which "see" only the movement of the fixed portion of the disposable. Such differential measurement systems allow subtraction of movement of the disposable as might be caused by the pumping mechanism from the pressure associated movement of the target. The optical pressure sensing system described above with respect to FIG. 6 can use an array of photosensors in a linear package. Some of the photosensors can be arranged to detect the disposable "frame" movement.

Various functions and elements described herein may be partitioned differently from those shown without departing from the spirit and scope of the invention. Various modifications to these embodiments will be readily apparent to those skilled in the art, and generic principles defined herein may be applied to other embodiments. Thus, many changes and modifications may be made to the invention, by one having ordinary skill in the art, without departing from the spirit and scope of the invention.

A reference to an element in the singular is not intended to mean "one and only one" unless specifically stated, but rather "one or more." The term "some" refers to one or more. Underlined and/or italicized headings and subheadings are used for convenience only, do not limit the invention, and are not referred to in connection with the interpretation of the description of the invention. All structural and functional equivalents to the elements of the various embodiments of the invention described throughout this disclosure that are known or later conic to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

What is claimed is:

1. A non-contact pressure sensing system for measuring either positive or negative fluid pressures within an isolated fluid pathway using a chamber incorporated within the isolated fluid pathway and connected to a fluid supply pump, the system comprising:
   a sensor base coupled to a pump and having at least one sensing arrangement being stationary with respect to the sensor base, the sensing arrangement configured to generate a measuring signal indicative of a sensed measurement variable;
   a measurement circuit electrically connected to the sensing arrangement to receive the measuring signal;
   a chamber or housing configured for attaching to the sensor base, the chamber having:
      a fluid inlet and a fluid outlet, and
      a movable element configured to move with changes in fluid pressure within the chamber and thereby cause a change in the sensed measurement variable without contacting the sensing arrangement, the amount of movement of the movable element being related to the amount of change in fluid pressure.

2. The system of claim 1, wherein the movable element is nonflexing when subjected to a nonzero fluid pressure.

3. The system of claim 1, wherein the fluid supply pump is an intravenous pump.

4. The system of claim 1, wherein the chamber is a housing that is configured to receive an IV fluid for measuring pressure of the IV fluid.

5. The system of claim 1, wherein the chamber is a cassette configured to hold an IV fluid being dispensed to a patient.

6. The system of claim 5, wherein the cassette is a disposable IV cassette.

7. The system of claim 1, wherein the movable element moves toward the sensing arrangement when the fluid pressure increases and away from the sensing arrangement when the fluid pressures decreases.

8. The system of claim 1 wherein the movable element is configured to be responsive to both positive and negative fluid pressures within the cassette without being preloaded.

9. The system of claim 5, wherein the sensor base is connected to the pump via at least one spring to cause the sensor base to exert a force against the cassette when the cassette is mated with the based.

10. The system of claim 1 further comprising a sensing measurement varying element coupled to the movable element and configured to cause the change in the sensed measurement variable.

11. The system of claim 10, wherein:
    the sensing arrangement comprises a first plate and a second plate coupled to the sensor base;
    the sensing measurement varying element comprises a conductive layer; and
    the sensed measurement variable comprises a capacitance between the first and second plates.

12. The system of claim 8 further comprising a printed circuit substrate, wherein the first and second plates and the measurement circuit are disposed on the printed circuit substrate.

13. The system of claim 10, wherein:
    the sensing arrangement comprises a light source and a light detector coupled to the sensor base;
    the sensing measurement varying element comprises an optical attenuator; and
    the sensed measurement variable comprises an intensity of light received at the light detector.

14. The system of claim 13, the optical attenuator having a thickness in a travel direction of the light, wherein the thickness varies along a movement direction of the optical attenuator.

15. The system of claim 10, wherein:
    the sensing arrangement comprises a magnetic field sensor coupled to the sensor base;
    the sensing measurement varying element comprises a magnet; and
    the sensed measurement variable comprises a strength of a magnetic field at the magnetic field sensor.

16. The system of claim 15, wherein the magnetic field sensor is a hall-effect sensor, a magnetoresistive sensor, or a fluxgate magnetometer.

17. A cassette configured for attaching to a fluid supply pump, the cassette comprising:
a pumping chamber having a fluid inlet and a fluid outlet and configured to receive a fluid from a fluid storage unit via the fluid inlet, and
a diaphragm structure coupled to the pumping chamber, the diaphragm structure comprising a movable element configured to move with changes in fluid pressure within the pumping chamber and thereby cause a change in a sensed measurement variable sensed by at least one sensing arrangement coupled to the fluid supply pump without contacting the sensing arrangement, the amount of movement of the movable element being related to the amount of change in fluid pressure.

18. The cassette of claim 17, the diaphragm structure comprises a deformable element connected to the perimeter of the movable element and configured to deform in response to the changes in the fluid pressure within the pumping chamber.

19. The cassette of claim 18, wherein the deformable element has a sigmoid-shaped cross section.

20. The cassette of claim 18, wherein the movable element is nonflexing when subjected to a nonzero fluid pressure.

21. The cassette of claim 18, wherein the movable element and the deformable element comprise a same material and formed in a single mold.

22. The cassette of claim 21, wherein the same material includes a polycarbonate.

23. The cassette of claim 18, wherein the movable element and the deformable element comprise different materials and are co-molded together.

24. The cassette of claim 23, wherein the deformable element comprises a thermoplastic elastomer.

25. The cassette of claim 18, wherein the diaphragm structure comprises a cavity disposed between the pumping chamber and the movable element, the cavity in fluidic communication with the fluid within the pumping chamber.

26. The cassette of claim 17 further comprising a sensor measurement varying element coupled to the movable element, wherein the sensor measurement varying element comprises a conductive layer, and the sensed measurement variable comprises a capacitance between two plates.

27. The cassette of claim 17 further comprising a sensor measurement varying element coupled to the movable element, wherein the sensor measurement varying element comprises an optical attenuator, and the sensed measurement variable comprises an intensity of light measured by a light detector.

28. The cassette of claim 17 further comprising a sensor measurement varying element, wherein the sensor measurement varying element comprises a magnet, and the sensed measurement variable comprises a strength of a magnetic field measured by a magnetic field sensor.

29. A method of measuring pressure of fluid in a disposable IV set connected to a fluid supply pump, the method comprising:
providing at least one sensing arrangement coupled to the fluid supply pump;
providing a chamber having a movable element configured to move with the movable element in response to changes in fluid pressure within the disposable IV set and thereby cause a change in a sensed measurement variable associated with the sensing arrangement without contacting the sensing arrangement;
generating a measuring signal indicative of the sensed measurement variable; and
determining the fluid pressure within the disposable IV set based on the measuring signal.

30. The method of claim 29 further comprising measuring a negative pressure within the disposable IV set without having the sensing arrangement positively biased.

31. The method of claim 29 further comprising providing a sensor measurement varying element coupled to the movable element.

32. The method of claim 31, wherein:
the sensing arrangement comprises a first plate and a second plate;
the sensing measurement varying element comprises a conductive layer; and
the sensed measurement variable comprises a capacitance between the first and second plates.

33. The method of claim 31, wherein:
the sensing arrangement comprises a light source and a light detector;
the sensing measurement varying element comprises an optical attenuator; and
the sensed measurement variable comprises an intensity of light received at the light detector.

34. The method of claim 31, wherein:
the sensing arrangement comprises a magnetic field sensor;
the sensing measurement varying element comprises a magnet; and
the sensed measurement variable comprises a strength of a magnetic field at the magnetic field sensor.

* * * * *

UNITED STATES PATENT AND TRADEMARK OFFICE
CERTIFICATE OF CORRECTION

PATENT NO. : 8,096,186 B2
APPLICATION NO. : 12/731001
DATED : January 17, 2012
INVENTOR(S) : Robert D. Butterfield It is certified that error appears in the above-identified patent and that said Letters Patent is hereby corrected as shown below:

IN THE CLAIMS:

In Column 14, Line 13: Claim 3: Add -- (IV) -- after "an intravenous"

Signed and Sealed this
Eighteenth Day of September, 2012

David J. Kappos
*Director of the United States Patent and Trademark Office*